United States Patent
Marszalek

(10) Patent No.: US 6,278,282 B1
(45) Date of Patent: Aug. 21, 2001

(54) METHOD AND SYSTEM FOR DETERMINING OIL QUALITY

(75) Inventor: Gary A. Marszalek, South Lyon, MI (US)

(73) Assignee: Detroit Diesel Corporation, Detroit, MI (US)

( * ) Notice: Subject to any disclaimer, the term of this patent is extended or adjusted under 35 U.S.C. 154(b) by 0 days.

(21) Appl. No.: 09/413,771

(22) Filed: Oct. 7, 1999

(51) Int. Cl.[7] .......................... G01R 27/26; G01R 27/08
(52) U.S. Cl. .................. 324/663; 324/698; 324/709; 324/713; 324/683
(58) Field of Search .................. 324/658, 663, 324/672, 698, 699, 709, 713, 683, 553; 340/603

(56) References Cited

U.S. PATENT DOCUMENTS

| | | |
|---|---|---|
| 3,753,092 | 8/1973 | Ludlow et al. . |
| 3,774,238 | 11/1973 | Hardway, Jr. . |
| 4,058,766 | 11/1977 | Vogel et al. . |
| 4,258,422 | 3/1981 | Dougherty et al. . |
| 4,322,678 | 3/1982 | Capots et al. . |
| 4,646,070 * | 2/1987 | Yasuhara ........................ 340/603 |
| 4,857,829 * | 8/1989 | Sagae et al. ..................... 324/698 |
| 4,924,702 | 5/1990 | Park . |
| 5,262,732 | 11/1993 | Dickert et al. . |
| 5,274,335 | 12/1993 | Wang et al. . |
| 5,540,086 | 7/1996 | Park et al. . |
| 5,604,441 | 2/1997 | Freese et al. . |
| 5,900,810 | 5/1999 | Park et al. . |
| 5,907,278 | 5/1999 | Park et al. . |
| 5,929,754 | 7/1999 | Park et al. . |
| 5,973,503 | 10/1999 | Kuipers et al. . |

* cited by examiner

Primary Examiner—Safet Metjahic
Assistant Examiner—Anjan K Deb
(74) Attorney, Agent, or Firm—Brooks & Kushman P.C.

(57) ABSTRACT

A method for determining quality of lubricating oil using electrodes in contact with the oil includes applying a potential having a first amplitude to the electrodes, wherein the first amplitude is sufficiently low such that substantially no solution current will flow; determining a first voltage phase lag with respect to the potential when the potential has the first amplitude; increasing amplitude of the potential to a second amplitude at which solution current flows; determining a second voltage phase lag with respect to the potential when the potential has the second amplitude; and determining the quality of the oil based on the voltage phase lags. A system for practicing the method is also provided.

10 Claims, 3 Drawing Sheets

METHOD AND SYSTEM FOR DETERMINING OIL QUALITY

TECHNICAL FIELD

The invention relates to a method and system for determining oil quality, wherein the method and system accurately account for solution current.

BACKGROUND ART

Lubricating oil improves the efficiency and durability of such systems as internal combustion engines, compressors, pumps and gear boxes. The presence of contaminants in the oil, however, significantly affects the performance of the oil. Such contaminants include soot, dissolved gases, dissolved liquids, emulsified liquids, and particles resulting from system wear.

Many methods and systems have been developed to detect contaminants in oil. One prior system, for example, includes a capacitive oil deterioration sensor that is used to determine the dielectric constant of engine oil based on the capacitive reactance of the oil. The theory behind this sensor is that the dielectric constant of the oil is related to the concentration of contaminants in the oil. Assuming the oil is a perfect insulator, the capacitive reactance $X_c$ of the oil can be expressed as:

$$X_c = 1/(2\pi fC),$$

where f is the frequency of a potential applied across the sensor, and C is the capacitance of the oil.

While the capacitive reactance can be measured with little error in non-polar oil, measurement error increases with increasing conductivity of the oil due to solution current flowing through the oil.

Generally, newly refined base oil stock is a non-polar solution. When it is formulated for lubricating oil, various additives are added to improve performance and extend the useful life of the oil. Many of these additives, however, are polar and increase the conductivity of the oil. Conductivity of the oil further increases with increasing temperature. Even as "new" oil reaches operating temperatures, minor solution current can be detected. Solution current also increases as contaminants increase in the oil during use.

Furthermore, prior art methods and systems typically utilize an unbalanced alternating current (AC) or static direct current (DC) potential that causes migration of polar contaminants toward oppositely charged sensor electrodes. Eventually, this contaminant migration results in build up of contaminants on the electrodes, which contributes to erroneous capacitive reactance measurements of the oil.

DISCLOSURE OF INVENTION

The invention overcomes the shortcomings of the prior art by providing an improved method and system for determining oil quality, wherein the method and system accurately account for solution current.

Under the invention, a method for determining quality of lubricating oil using electrodes in contact with the oil includes applying a potential having a first amplitude to the electrodes, wherein the first amplitude is sufficiently low such that substantially no solution current will flow; determining a first voltage phase lag with respect to the potential when the potential has the first amplitude; increasing amplitude of the potential to a second amplitude at which solution current flows; determining a second voltage phase lag with respect to the potential when the potential has the second amplitude; and determining the quality of the oil based on the voltage phase lags.

Preferably, the potential is a symmetrically balanced, time-varying potential so that the electrodes experience a substantially zero net charge. Advantageously, then, contaminant build-up on the electrodes may be substantially reduced.

Further under the invention, a method for determining quality of lubricating oil includes applying a potential having a first amplitude across electrodes in contact with the oil, wherein the first amplitude is sufficiently low such that substantially no solution current flows; increasing amplitude of the potential to a second amplitude at which detectable solution current begins to flow; and determining the quality of the oil based on the second amplitude.

Preferably, the method further includes monitoring voltage phase lag with respect to the potential. Advantageously, by monitoring voltage phase lag, the point at which detectable solution current begins to flow, as well as the relative degree of solution current, may be determined.

A system for determining quality of lubricating oil includes a sensor having first and second electrodes adapted to contact the oil. The system further includes a microprocessor in communication with the sensor. The microprocessor includes instructions for applying a potential having a first amplitude to the electrodes, wherein the first amplitude is sufficiently low such that substantially no solution current flows; instructions for determining a first voltage phase lag with respect to the potential when the potential has the first amplitude; instructions for increasing amplitude of the potential to a second amplitude at which solution current flows; instructions for determining a second voltage phase lag with respect to the potential when the potential has the second amplitude; and instructions for determining the quality of the oil based on the voltage phase lags.

Further under the invention, a system for determining quality of lubricating oil includes first and second electrodes adapted to contact the oil. The system further includes a microprocessor in communication with the electrodes. The microprocessor includes instructions for applying a potential having a first amplitude to electrodes in contact with the oil, wherein the first amplitude is sufficiently low such that substantially no solution current flows; instructions for increasing amplitude of the potential to a second amplitude at which detectable solution current begins to flow; and instructions for determining the quality of the oil based on the second amplitude.

These and other objects, features and advantages of the invention are readily apparent from the following detailed description of the best modes for carrying out the invention when taken in conjunction with the accompanying drawings.

BEST MODE FOR CARRYING OUT THE INVENTION

Figure 1:
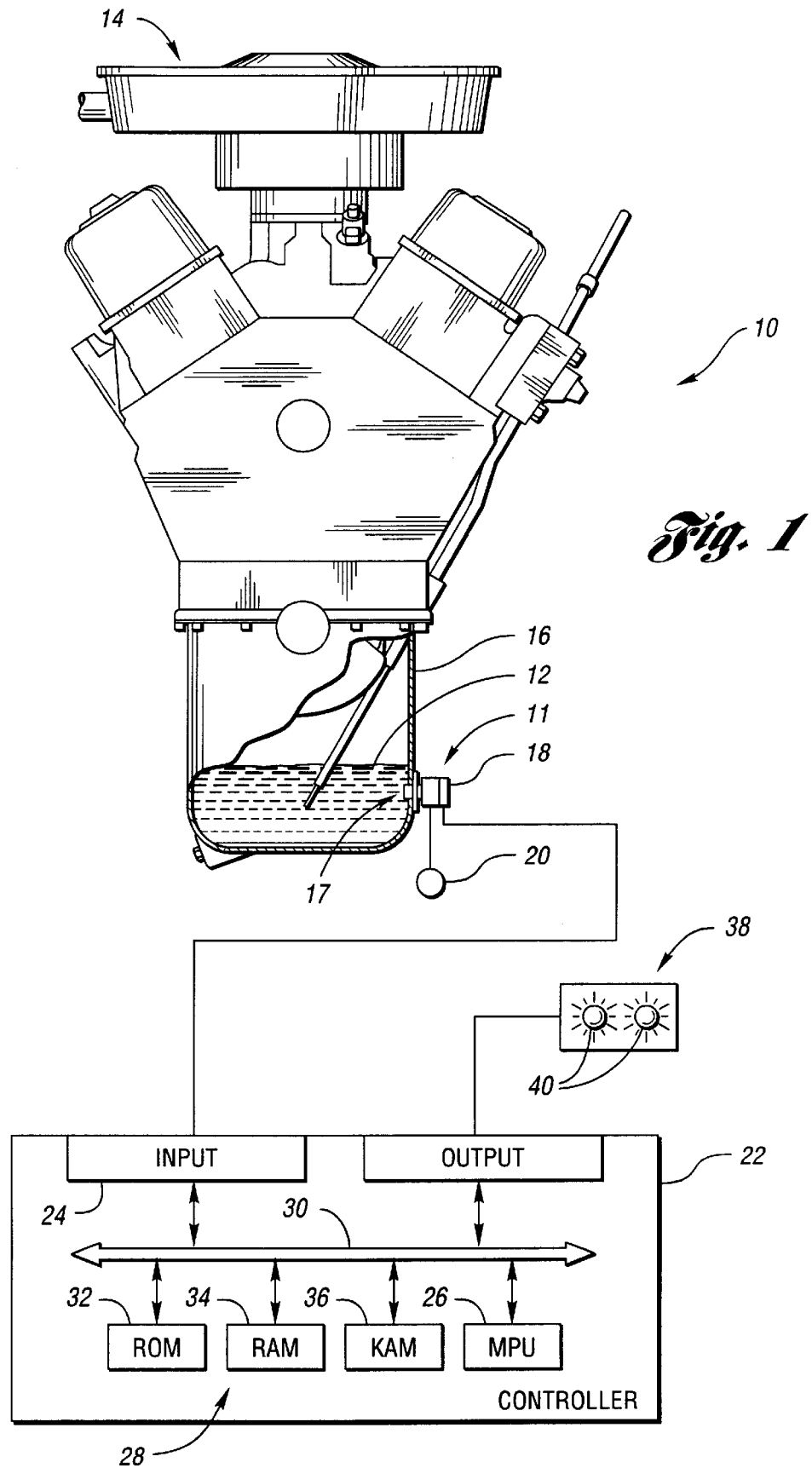
FIG. 1 is a schematic diagram of a system for determining oil quality according to the invention, and the system includes a sensor mounted to an oil reservoir of a motor vehicle engine and having a control circuit.

FIG. 1 shows a system 10 according to the invention for determining quality of lubricating oil 12 in a motor vehicle engine 14, or other suitable arrangement such as a compressor, pump or gear box. The system 10 includes a sensor 11 adapted to be mounted to an oil reservoir 16 of the engine 14. The sensor 11 includes two spaced electrodes 17 adapted to be immersed in the oil 12, and a control circuit 18. When the electrodes 17 are joined by the oil 12, which is generally a dielectric material, a capacitor is formed.

As further shown in FIG. 1, the sensor 11 is connected to a power source 20 for applying a time-varying potential, such as an AC potential, across the electrodes 17. For example, the power source 20 may include a motor vehicle battery and an AC converter. Preferably, the power source 20 cooperates with the control circuit 18, as explained below in greater detail, to provide a substantially symmetrically balanced sinusoidal AC potential across the electrodes 17 such that substantially no DC bias is created across the electrodes 17. Such a potential reduces or eliminates contaminant build up on the electrodes 17 as explained below in greater detail. Alternatively, the power source 20 may provide any suitable time-varying potential such as a triangular or square waveform potential such that substantially no DC bias is created across the electrodes 17.

The system 10 further includes a first controller 22 in electrical communication with the sensor 11 via input ports 24 of the first controller 22. The first controller 22 preferably includes a microprocessor 26 in communication with various computer readable storage media 28 via data and control bus 30. The computer readable storage media 28 may include any of a number of known devices which function as a read-only memory (ROM) 32, random access memory (RAM) 34, keep-alive memory (KAM) 36, and the like. The computer readable storage media 28 may include data representing program instructions (software), calibrations, operating variables and the like that are used in conjunction with associated hardware to effect control of the system 10. The computer readable storage media 28 may be implemented by any of a number of known physical devices capable of storing data representing instructions executable via a computer such as first controller 22. Known devices may include, but are not limited to, PROM, EPROM, EEPROM, flash memory, and the like in addition to magnetic, optical, and combination media capable of temporary or permanent data storage.

In operation, the first controller 22 receives signals from the sensor 11 via input ports 24, and generates output signals that may be provided to various actuators and/or components, such as a display device 38, which may include various indicators such as lights 40 to communicate information relative to oil quality to the operator of the vehicle. Of course, alphanumeric, audio, video, or other displays or indicators may be utilized if desired. In a preferred embodiment, the first controller 22 is a Detroit Diesel Electronic Controller (DDEC) available from Detroit Diesel Corporation, Detroit, Mich.

Figure 2:
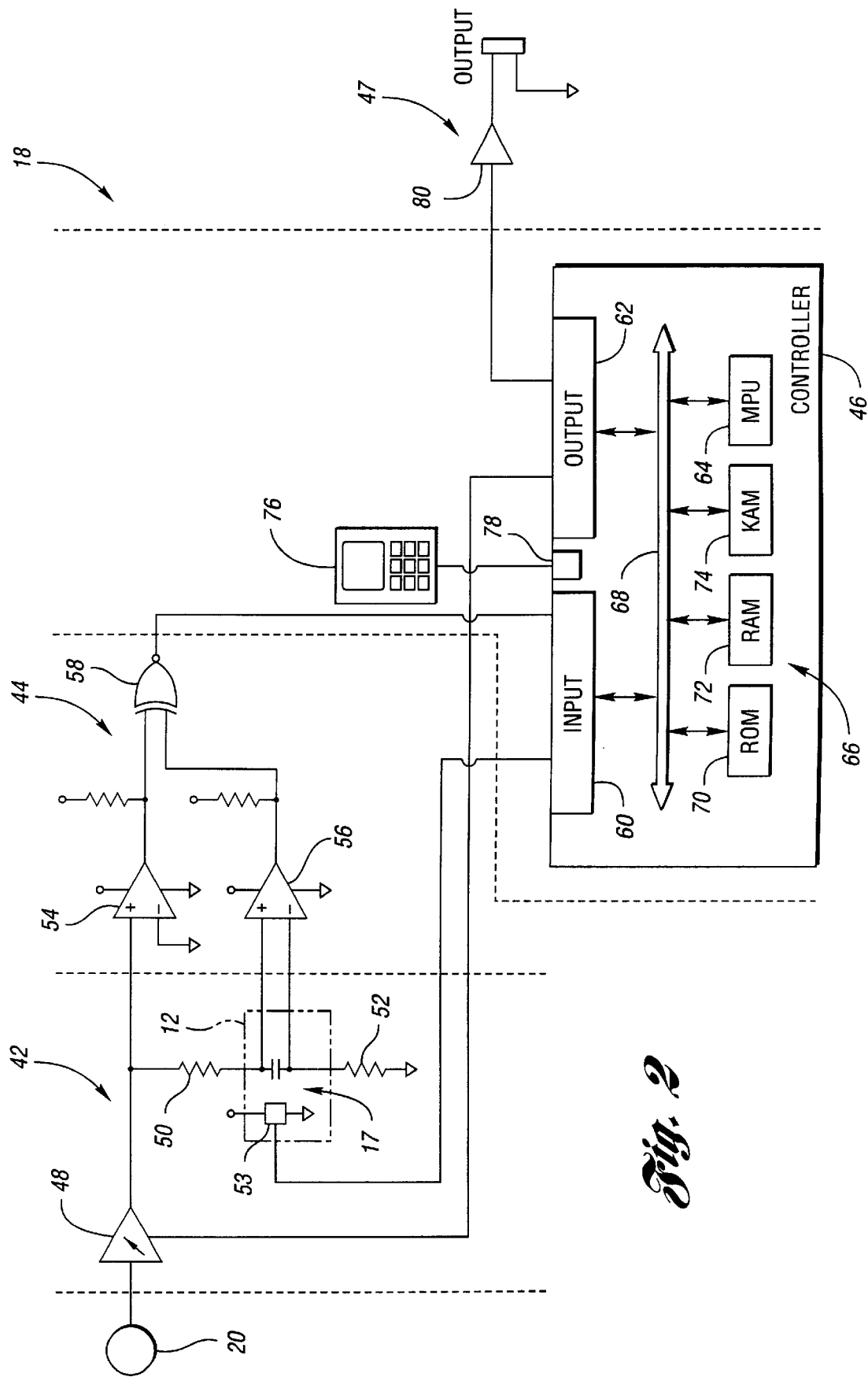
FIG. 2 is a schematic diagram of one embodiment of the control circuit.

While many control circuits having various hardware and software components can be utilized with the system 10, a simplified schematic representation of an exemplary embodiment of the control circuit 18 is shown in FIG. 2. The control circuit 18 includes a drive controlling portion 42, a signal comparison portion 44, a second controller or micro-controller 46, and a scaling portion 47.

The drive controlling portion 42 is connected to the power source 20, and is used to control the potential applied across the electrodes 17. The drive controlling portion 42 includes a first operational amplifier or voltage controlled amplifier (VCA) 48 connected to the micro-controller 46, and first and second resistors 50 and 52 for balancing the applied potential across the electrodes 17.

A temperature sensor 53 is also preferably disposed proximate the electrodes 17 for sensing temperature of the oil 12. The temperature sensor 53 provides a temperature output signal to the micro-controller 46, which adjusts output from the sensor 11 as explained below in greater detail.

The signal comparison portion 44 includes first and second comparators 54 and 56, respectively, and an Exclusive-NOR gate 58. The first comparator 54 is connected to the VCA 48, and preferably generates a first square-wave output signal representative of the applied potential. The second comparator 56 is connected across the electrodes 17, and preferably generates a second square-wave output signal representative of the voltage across the electrodes 17. The first and second output signals are input to the gate 58, which generates a pulse-width modulated (PWM) output signal that is indicative of the phase difference between the first and second output signals. In other words, the PWM output signal is indicative of the voltage phase lag with respect to the applied potential.

The micro-controller 46 is in electrical communication with the temperature sensor 53 and the gate 58 via input ports 60. Furthermore, the micro-controller 46 is in electrical communication with the scaling portion 47 and the VCA 48 via output ports 62. The micro-controller 46 preferably includes a microprocessor 64 in communication with various computer readable storage media 66 via data and control bus 68. The computer readable storage media 66 may include any of a number of known devices which function as a read-only memory (ROM) 70, random access memory (RAM) 72, keep-alive memory (KAM) 74, and the like. The computer readable storage media 66 may include data representing program instructions (software), calibrations, operating variables and the like that are used in conjunction with associated hardware to effect control of the control circuit 18 and system 10. The computer readable storage media 66 may be implemented by any of a number of known physical devices capable of storing data representing instructions executable via a computer such as micro-controller 46. Known devices may include, but are not limited to, PROM, EPROM, EEPROM, flash memory, and the like in addition to magnetic, optical, and combination media capable of temporary or permanent data storage.

In operation, the micro-controller 46 may be used to control the potential applied across the electrodes 17. Furthermore, the micro-controller 46 receives the temperature output signal from the temperature sensor 53, and the PWM output signal from the gate 58. The micro-controller 46 then generates an output signal, which is calibrated to compensate for temperature of the oil 12, and has an amplitude related to the phase difference between the first and second output signals of the first and second comparators 54 and 56, respectively.

A data, diagnostics, and programming interface 76 may also be selectively connected to micro-controller 46 via a plug 78 to exchange various information therebetween. Interface 76 may be used to change values within the computer readable storage media 66, such as configuration settings, calibration variables, control logic, and the like.

The scaling portion 47 includes a second operational amplifier 80 for adjusting scaling voltages indicative of clean and contaminated oil. The scaling portion 47 receives the output signal from the micro-controller 46, adjusts the signal as necessary, and provides a scaled output signal to the first controller 22, which processes the signal as described below in greater detail. Alternatively, the micro-controller 46 may perform any scaling functions that may be required.

Although the electrodes 17 form a capacitor when immersed in the oil 12, the sensor 11 may exhibit some form of leakage current or solution current due to polar additives and/or contaminants in the oil 12. The additives and/or contaminants carry charge through the oil 12 from one electrode 17 to the other electrode 17, thereby creating the solution current. There is a minimum voltage requirement, however, that must be exceeded before charge will transfer from one of the electrodes 17 to the additives and/or contaminants in the oil 12 such that the solution current will flow. This minimum voltage requirement, known as the redox potential, varies with the concentration of additives and/or contaminants in the oil 12.

Prior art sensors that attempt to measure capacitive reactance of oil fail to adequately account for solution current. Solution current, which can be schematically modeled as a variable resistance in parallel with a particular sensor, results in the sensor measuring total impedance of the oil and not just the capacitive reactance of the oil. Capacitive reactance $X_c$ can be expressed as:

$$X_c = 1/(2\pi fC),$$

where f is the frequency of a potential applied across the sensor, and C is the capacitance of the oil.

Total impedance Z, for an oil resistance R and a capacitive reactance $X_c$ in parallel, can be expressed as:

$$Z = RX_c/\sqrt{(R^2 + X_c^2)}$$

Comparing the above equations at various oil resistance values reveals how solution current can dramatically affect measured results of such prior art sensors.

Under the invention, an improved method for determining oil quality is provided, and the method accounts for solution current by determining voltage phase lag with respect to an applied potential. In an ideal, purely capacitive circuit, current leads voltage by an angle of 90 degrees. As described above, however, the sensor 11 may exhibit some form of solution current due to polar additives and/or contaminants. This solution current may be schematically modeled as a variable resistance in parallel with the electrodes 17. Furthermore, in an ideal, purely resistive circuit, current and voltage are in phase. Thus, by monitoring the degree of voltage phase lag with respect to applied potential, the presence of solution current can be detected.

Figure 3:
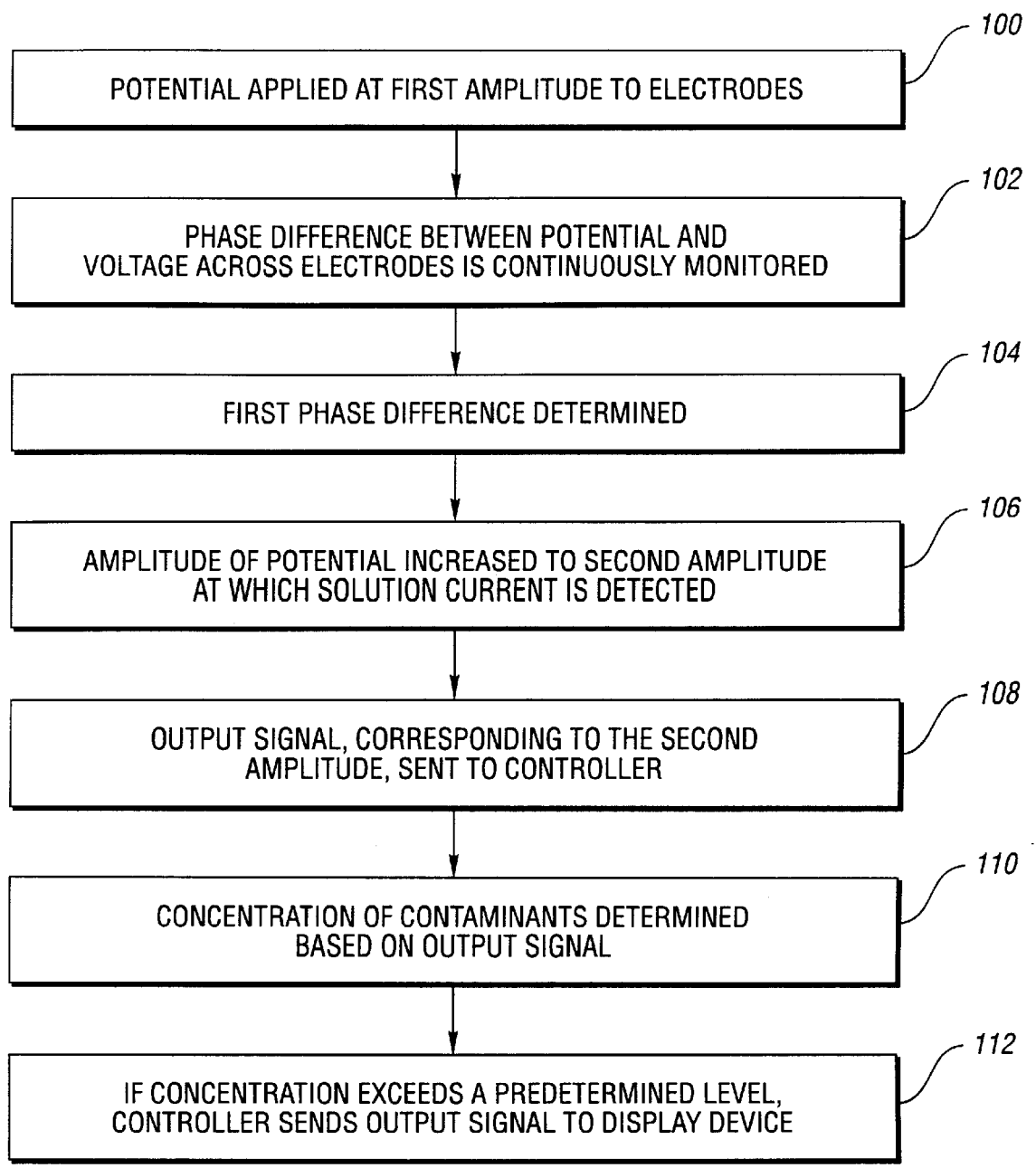
FIG. 3 is a flow chart illustrating operation of a system or method according to the invention for determining oil quality.

FIG. 3 is a flow chart illustrating operation of a method or system, such as the system 10, for determining oil quality based on solution current. At step 100, a time-varying potential having a first amplitude and a predetermined frequency is applied across the electrodes 17 using the power source 20 and control circuit 18. The first amplitude is preferably selected such that the first amplitude is below the redox potential of the oil 12 when the oil 12 has a significant concentration of contaminants, in order to substantially reduce or eliminate solution current. At step 102, phase difference between the applied potential and the voltage across the electrodes 17 may be continuously monitored using the control circuit 18. At step 104, an initial or first phase difference between the applied potential and the voltage across the electrodes 17 is determined when the potential has the first amplitude. This first phase difference, or first voltage phase lag, may be used by the micro-controller 46 as a reference point to indicate phase difference associated with factors other than solution current, such as error capacitance resulting from contaminant build-up on the electrodes 17.

At step 106, the amplitude of the potential is gradually increased from the first amplitude to a second amplitude at which solution current is first detected. When solution current begins to flow, phase difference between the applied potential and the voltage across the electrodes 17 will decrease to a second phase difference, or second voltage phase lag. An output signal is then sent from the sensor 11 to the first controller 22 corresponding to the second amplitude of the potential, as indicated at step 108.

Next, the quality of the oil 12 may be determined by the first controller 22 based on the output signal from the sensor 11, as indicated at step 110. For example, the first controller 22 may compare the output signal from the sensor 11 to a table of predetermined voltage values that correspond with various contaminant concentrations or oil qualities. Because redox potential decreases as the concentration of contaminants increases, the lower the second amplitude of the potential, the greater the concentration of contaminants. If the concentration of contaminants exceeds a predetermined level, the first controller 22 preferably sends an output signal to the display device 38 as indicated at step 112. The display device 38 may then be used to communicate information regarding oil quality to the operator of the vehicle.

It is to be understood that the first controller 22 may be configured to perform some or all of the functions of the micro-controller 46. Similarly, the micro-controller 46 may be configured to perform some or all of the functions of the first controller 22.

Alternatively or supplementally, the quality of the oil 12 may be determined by comparing the first and second phase differences. Because the second phase difference will decrease with increasing concentration of contaminants, the difference between the first and second phase differences will increase with increasing concentration of contaminants. Under this approach, however, the second amplitude of the potential may be any amplitude at or above the redox potential of the oil 12.

Because the power source 20 and control circuit 18 preferably provide a symmetrically balanced, purely AC potential, the electrodes 17 experience a substantially zero net charge. As a result, migration of polar contaminants is substantially reduced. Thus, contaminant buildup on the electrodes 17, which is manifested as error capacitance, is substantially reduced. Additionally, by applying the potential during the measurement cycle only, contaminant migration can be further reduced.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method for determining quality of lubricating oil using electrodes in contact with the oil, the method comprising:

applying a potential having a first amplitude to the electrodes, wherein the first amplitude is sufficiently low such that substantially no solution current flows;

determining a first voltage phase lag with respect to the potential when the potential has the first amplitude;

increasing amplitude of the potential to a second amplitude at which solution current flows;

determining a second voltage phase lag with respect to the potential when the potential has the second amplitude; and determining the quality of the oil based on the voltage phase lags.

2. The method of claim 1 wherein applying a first potential comprises applying a substantially symmetrically balanced time-varying potential.

3. A method for determining quality of lubricating oil, the method comprising:

applying a potential having a first amplitude to electrodes in contact with the oil, wherein the first amplitude is sufficiently low such that substantially no solution current flows;

increasing amplitude of the potential to a second amplitude at which detectable solution current begins to flow; and determining the quality of the oil based on the second amplitude.

4. The method of claim 3 wherein applying a potential comprises applying a substantially symmetrically balanced time-varying potential.

5. The method of claim 3 further comprising monitoring voltage phase lag with respect to the potential in order to determine when detectable solution current begins to flow.

6. A method for determining quality of lubricating oil, the method comprising:

positioning first and second electrodes in the oil;

applying a potential having a first amplitude to the electrodes, wherein the first amplitude is below a redox potential of the oil;

determining a first voltage phase lag with respect to the potential when the potential has the first amplitude;

increasing amplitude of the potential to a second amplitude above the redox potential;

determining a second voltage phase lag with respect to the potential when the potential has the second amplitude;

determining solution current based on the voltage phase lags; and determining the quality of the oil based on the solution current.

7. A system for determining quality of lubricating oil, the system comprising:

first and second electrodes adapted to contact the oil; and a microprocessor in communication with the electrodes, the microprocessor including instructions for applying a potential having a first amplitude to the electrodes, wherein the first amplitude is sufficiently low such that substantially no solution current flows; instructions for determining a first voltage phase lag with respect to the potential when the potential has the first amplitude; instructions for increasing amplitude of the potential to a second amplitude at which solution current flows; instructions for determining a second voltage phase lag with respect to the potential when the potential has the second amplitude; and instructions for determining the quality of the oil based on the voltage phase lags.

8. A system for determining quality of lubricating oil, the system comprising:

first and second electrodes adapted to contact the oil; and a microprocessor in communication with the electrodes, the microprocessor including instructions for applying a potential having a first amplitude to electrodes in contact with the oil, wherein the first amplitude is sufficiently low such that substantially no solution current flows; instructions for increasing amplitude of the potential to a second amplitude at which detectable solution current begins to flow; and instructions for determining the quality of the oil based on the second amplitude.

9. A computer readable storage medium having information stored thereon representing instructions executable by a controller to determine quality of lubricating oil using electrodes in contact with the oil, the computer readable storage medium comprising:

instructions for applying a potential having a first amplitude to the electrodes, wherein the first amplitude is sufficiently low such that substantially no solution current flows;

instructions for determining a first voltage phase lag with respect to the potential when the potential has the first amplitude;

instructions for increasing amplitude of the potential to a second amplitude at which solution current flows;

instructions for determining a second voltage phase lag with respect to the potential when the potential has the second amplitude; and instructions for determining the quality of the oil based on the voltage phase lags.

10. A computer readable storage medium having information stored thereon representing instructions executable by a controller to determine quality of lubricating oil using electrodes in contact with the oil, the computer readable storage medium comprising:

instructions for applying a potential having a first amplitude to the electrodes, wherein the first amplitude is sufficiently low such that substantially no solution current flows;

instructions for increasing amplitude of the potential to a second amplitude at which detectable solution current begins to flow; and instructions for determining the quality of the oil based on the second amplitude.

* * * * *